(12) United States Patent
Kay et al.

(10) Patent No.: US 9,713,679 B2
(45) Date of Patent: Jul. 25, 2017

(54) APPARATUS FOR DELIVERING FOAM

(71) Applicant: BTG INTERNATIONAL LIMITED, London (GB)

(72) Inventors: Stuart Brian William Kay, Cambridgeshire (GB); Christopher John Hurlstone, Cambridgeshire (GB); Julian Richard Dixon, Cambridgeshire (GB); Andrew Gordon Pocock, Cambridgeshire (GB)

(73) Assignee: BTG INTERNATIONAL LIMITED, London (GB)

(*) Notice: Subject to any disclaimer, the term of this patent is extended or adjusted under 35 U.S.C. 154(b) by 0 days.

(21) Appl. No.: 14/878,588

(22) Filed: Oct. 8, 2015

(65) Prior Publication Data

US 2016/0114106 A1    Apr. 28, 2016

Related U.S. Application Data

(63) Continuation of application No. 13/137,796, filed on Sep. 14, 2011, now abandoned, which is a
(Continued)

(30) Foreign Application Priority Data

Dec. 3, 2003    (GB) .................................. 0327957.7

(51) Int. Cl.
*A61M 5/315* (2006.01)
*B01F 3/04* (2006.01)
(Continued)

(52) U.S. Cl.
CPC ...... *A61M 5/31511* (2013.01); *A61M 5/2053* (2013.01); *A61M 5/3129* (2013.01);
(Continued)

(58) Field of Classification Search
CPC .......... A61M 2005/1787; A61M 2005/31598; A61M 5/31596; A61M 2005/3132; A61M 5/19
(Continued)

(56) References Cited

U.S. PATENT DOCUMENTS 2,861,571 A    11/1958    Sandhage et al.
3,164,303 A *   1/1965    Trautmann ............ A61M 3/005
                                                         222/136
(Continued)

FOREIGN PATENT DOCUMENTS

DE    295 16 650 U1    12/1995
WO    WO 02/41872 A1    5/2002
WO    WO 03/099681 A1    12/2003

*Primary Examiner* — Phillip Gray
(74) *Attorney, Agent, or Firm* — Nixon & Vanderhye P.C.

(57) ABSTRACT

Syringe for dispensing foam having a syringe barrel, a nozzle and a bore to receive a syringe plunger having a front end and a back end. The syringe plunger includes at the front end thereof a waste container defined by a cylindrical side wall, a front end wall and a rear end wall, the walls being arranged such that an external cylindrical surface of the walls forms a seal with an internal surface of the syringe barrel. The waste container has an inlet aperture in the front end wall which is in communication with the syringe nozzle when the plunger is fully depressed into the syringe barrel. The waste container further has a hydrophobic vent in the rear end wall thereof which allows air to escape from the waste container while substantially preventing foam from escaping the waste container when the syringe is in use.

7 Claims, 5 Drawing Sheets

Related U.S. Application Data continuation of application No. 10/581,513, filed as application No. PCT/GB2004/005086 on Dec. 3, 2004, now abandoned.

(51) Int. Cl.

| | |
|---|---|
| *B01F 5/06* | (2006.01) |
| *B01F 13/00* | (2006.01) |
| *B01F 13/04* | (2006.01) |
| *A61M 5/20* | (2006.01) |
| *A61M 5/31* | (2006.01) |
| *A61M 5/38* | (2006.01) |
| *A61M 39/24* | (2006.01) |
| *B01F 15/00* | (2006.01) |

(52) U.S. Cl.
CPC .......... *A61M 5/3137* (2013.01); *A61M 5/385* (2013.01); *A61M 39/24* (2013.01); *B01F 3/04446* (2013.01); *B01F 5/0682* (2013.01); *B01F 5/0694* (2013.01); *B01F 13/002* (2013.01); *B01F 13/0023* (2013.01); *B01F 13/04* (2013.01); *B01F 15/00993* (2013.01); *A61M 2005/3114* (2013.01); *A61M 2005/3123* (2013.01); *A61M 2202/04* (2013.01); *B01F 15/00954* (2013.01); *B01F 2215/0034* (2013.01)

(58) Field of Classification Search
USPC ...................................... 604/518, 82, 85, 218
See application file for complete search history.

(56) References Cited

U.S. PATENT DOCUMENTS

| | | | |
|---|---|---|---|
| 3,376,999 | A | 4/1968 | De Hart et al. |
| 3,774,811 | A | 11/1973 | Staeman ........................ 222/190 |
| 4,968,301 | A | 11/1990 | Di Palma et al. ............ 604/132 |
| 5,181,909 | A * | 1/1993 | McFarlane ............ A61M 5/315 |
| | | | 604/191 |
| 5,273,190 | A | 12/1993 | Lund ............................. 222/83 |
| 5,395,325 | A | 3/1995 | Moreno et al. |
| 5,545,460 | A | 8/1996 | Tanaka et al. |
| 6,077,252 | A | 6/2000 | Siegel |
| 6,083,204 | A | 7/2000 | Malerba et al. |

\* cited by examiner

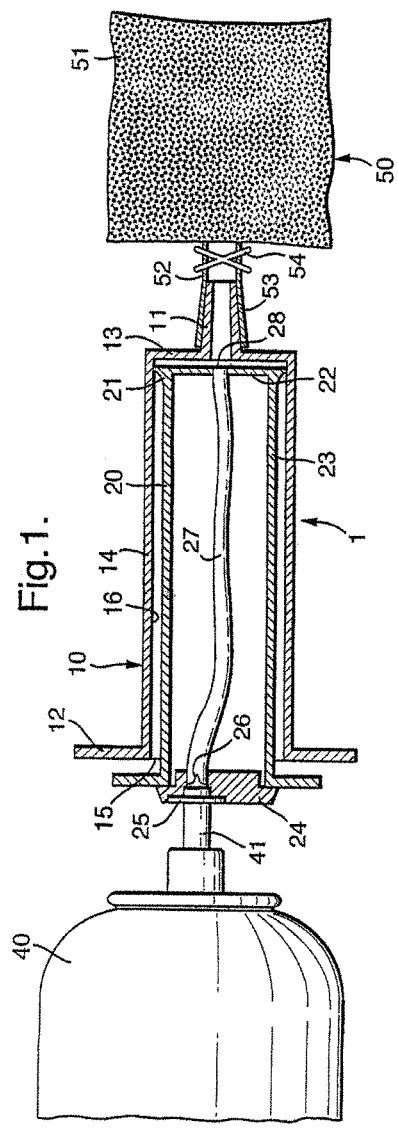
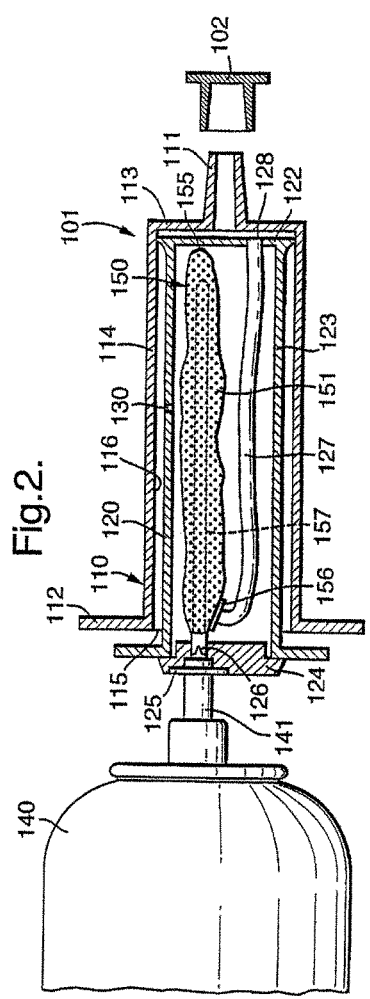

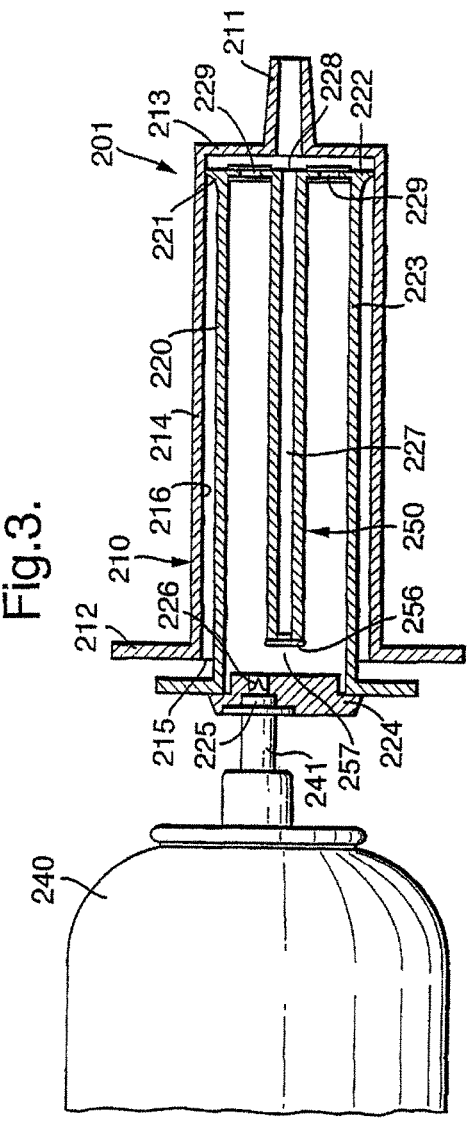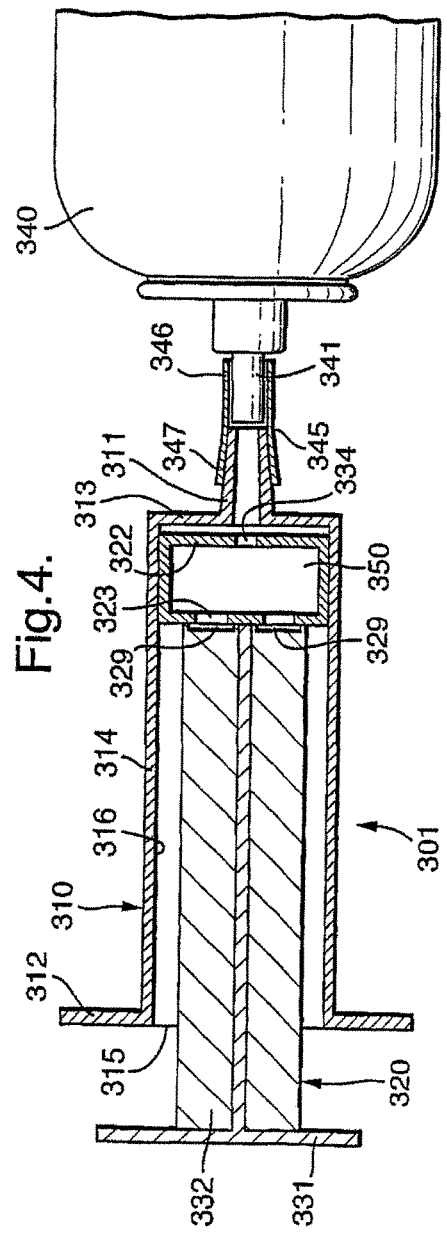

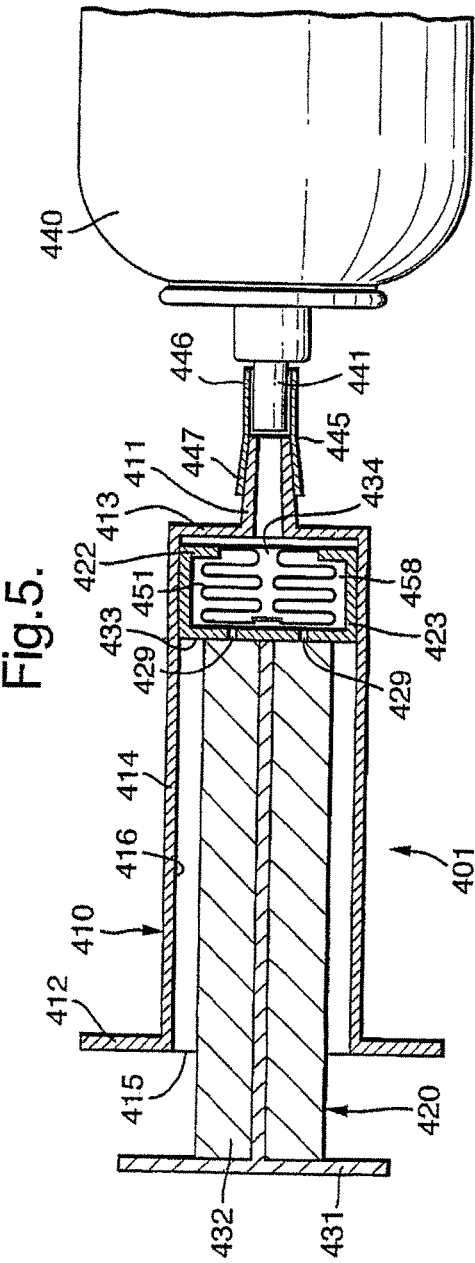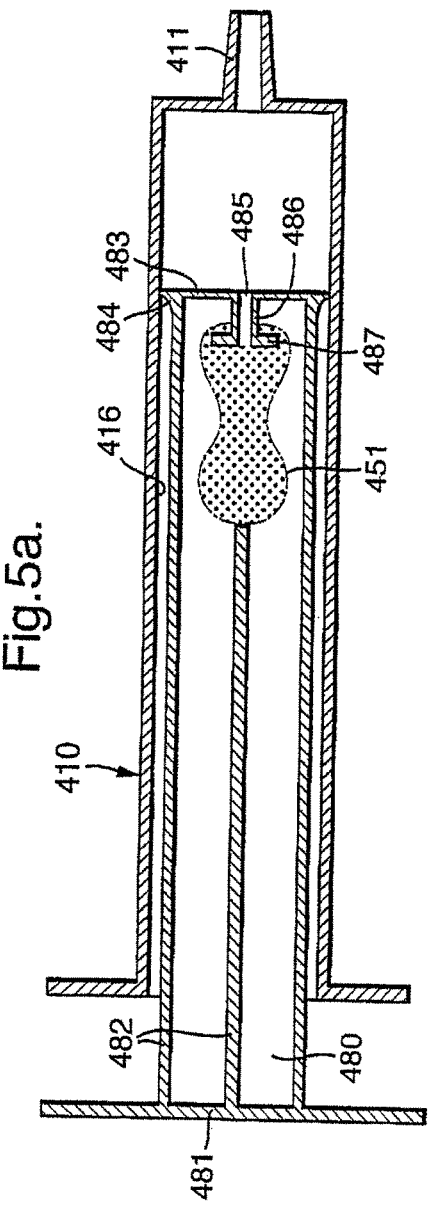

APPARATUS FOR DELIVERING FOAM

This application is a continuation of application Ser. No. 13/137,796 filed Sep. 14, 2011, (abandoned), which is a continuation of application Ser. No. 10/581,513 filed Aug. 2, 2006 (abandoned), which is a 371 of PCT/GB2004/005086 filed Dec. 3, 2004, which claims priority to British Patent Application No. 0327957.7 filed Dec. 3, 2003, the entire contents of each of which are hereby incorporated by reference.

The present invention relates to apparatus for delivering and to methods for filling such apparatus, e.g. from a source of foam such as a pressurized canister which generates foam by passing liquid and gas through a fine mesh. The invention is suitable in particular for a precision foam such as a sterile clinical grade therapeutic foam, e.g. for the treatment of varicose veins.

WO 00/72821 describes apparatus and methods for generating a foam for treatment of varicose veins. In one of the embodiments described in that patent application, foam is generated by pressurising a sclerosant liquid and a physiological gas in a canister and releasing the mixture through a mesh whereby a stable foam is produced suitable for injection into, varicosed blood vessels in sclerotherapy treatment. An apparatus is described which incorporates a three-way valve attached to the outlet of the foam generating canister. The first portion of foam generated by the canister tends to be of poor quality, and the valve allows this foam to be diverted to waste. The valve may then be switched over to feed foam to a syringe for use in treatment. The disclosure of WO 00/72821 is incorporated herein by reference.

A number of technical problems have been identified in the course of further development of the canister based system described in WO 00/72821. These include the following.

1. When the three-way valve is switched from the waste position to the fill position, there is a momentary dead time when the valve is closed to both outlet ports and flow is completely obstructed. When the valve is fully set to the fill position and the flow re-commences, the foam is initially of poor quality; the canister has effectively re-started its delivery of foam.
2. In a delivery device, such as a syringe, for administering foam to a patient, there is normally a dead space. In the case of a syringe, this is within the bore of the luer connector on the syringe. As foam is directed from the valve to the syringe and pushes the plunger of the syringe back, a large bubble tends to form adjacent the plunger, which may become incorporated within the foam and undermine its quality.
3. It is desirable to be able to inspect the foam and to determine when consistent, good quality foam is being generated, so as to check that foam with the correct properties is being directed into a patient's vein. In the apparatus described in WO 00/72821, the foam is observable in a transparent tube communicating between the canister and valve unit (ref 35 in FIGS. 10 and 11). A difficulty with this is that the foam which is observed is some way back from the foam being delivered. Therefore it is possible to observe adequate quality foam in the tube and still be delivering inadequate quality foam to the syringe.
4. The waste foam from tube 38 is not contained.
5. The use of a relatively long tube 35 joining the canister to the valve is wasteful, since a quantity of foam sufficient to fill the tube will always be wasted.
6. The system is somewhat dependant on the skill of the operator to consistently produce a syringe full of good quality foam.

Although these problems have been discussed above in connection with the system described in WO 00/72821, they may be applicable to other systems for generating and dispensing foam of various sorts, where a uniform foam product having consistent, predetermined properties is required. The contents of WO02/41872, which also relates to this field, is incorporated herein by reference.

A number of solutions to some or all of these problems have been devised. Some of these are described in a simultaneously filed patent application in the name of the applicant; these solutions relate in the main to features of a dispensing device which connects the foam source to a syringe, the syringe being the delivery device from which foam will ultimately be delivered for use. A number of solutions are described in the present application, which solutions are based more on modifications to the design of a syringe.

According to a first aspect of the invention, a syringe for dispensing foam comprises:
  (a) a syringe plunger having a front end and a back end;
  (b) a syringe barrel having a nozzle and a bore to receive the plunger;
  (c) wherein the plunger includes a foam inlet at the back end and a foam outlet at the front end, which inlet and outlet are in communication with each other; and
  (d) a one way valve permitting flow of foam into the inlet.

Preferably the plunger foam outlet is located adjacent the syringe nozzle. The plunger outlet may be provided in a projection from the seal end which projection extends into a bore of the syringe nozzle when the plunger is in a fully depressed state.

Also according to the first aspect of the invention, an apparatus for dispensing foam comprises a source of foam (e.g. a pressurised canister adapted for generating foam) and a syringe as described above. Preferably the source of foam includes an outlet of complementary form to the foam inlet of the plunger, and adapted to make a seal with the foam inlet.

Also according to the first aspect of the invention, an apparatus for dispensing foam comprises a syringe as described above together with a waste foam contain having an inlet with a connector of complementary form to the nozzle of the syringe. The waste foam container preferably has flexible walls (e.g. is a film or foil bag) and is substantially empty/airless before foam is dispensed into it. If the container is a flexible bag, the walls of the bag are preferably inextensible. The waste container may alternatively be rigid, in which case a vent is desirable which may take the form of a simple hole or alternatively a "hydrophobic vent", i.e. a vent having a filter of some sort which will allow gas but not liquid to pass.

Also according to the first aspect of the invention, an apparatus for dispensing foam comprises a source of foam, a syringe and a waste container as described above. The syringe, foam source and waste container may be supplied as a kit of separated elements, or two or more of these elements may be supplied ready assembled.

A method of dispensing foam according to the first aspect of the invention and using the above described apparatus comprises the steps of:
  (a) connecting the foam source to the plunger foam inlet (unless the source is supplied already so connected);
  (b) with the plunger fully depressed, generating a substantially continuous flow of foam from the said source and allowing an initial quantity of foam to flow from the plunger inlet through the plunger foam outlet and thence to exit from the syringe nozzle; and (c) without interrupting the flow of foam from the source, blocking the syringe nozzle and causing the plunger to move back—such that foam starts to fill the syringe barrel.

The method preferably comprises attaching a waste container to the syringe, or alternatively providing a syringe with a waste container fitted to it as described above. In this event, the waste container may be filled or substantially filled with the said initial quantity of foam in step (b) above, and may provide automatically the said syringe nozzle blocking step when so filled or substantially filled.

The syringe for dispensing foam as described may additionally comprise a waste container within an internal chamber defined by the plunger (or the internal plunger chamber or a part thereof may constitute the waste container), the container being in communication with the plunger foam inlet and having an outlet in communication with the plunger outlet. Preferably, the communication between the waste container outlet and the plunger outlet is via a pressure sensitive valve. The waste container may have the optional features described above, i.e. may have flexible walls or rigid walls and, if the latter, desirably has a vent which is either a hydrophobic vent or a small hole.

The invention also encompasses a syringe plunger for such a syringe, having the features described in the preceding paragraph.

The invention also encompasses such a syringe, together with a source of foam either in assembled form or in kit form.

With this syringe, the method of dispensing foam comprises:

(a) connecting the foam source to the plunger foam inlet (unless the source is supplied already so connected);

(b) generating a substantially continuous flow of foam from the said source and allowing an initial quantity of foam to flow from the plunger inlet into the waste container such as to fill or substantially fill the waste container; and (c) causing foam to flow from the plunger inlet to the plunger outlet and thence through the syringe nozzle for use.

Preferably, step (c) includes the step of causing sufficient back pressure to build up in the waste container to open the pressure sensitive valve thereby allowing flow of foam through the waste container outlet.

According to a second aspect of the invention, a syringe for dispensing foam comprises:

(a) a syringe plunger having an internal waste chamber with an inlet; and (b) a syringe barrel having a nozzle and a bore to receive the plunger; wherein the plunger inlet is in communication with the syringe nozzle.

Preferably the internal waste chamber is provided with a vent which may either be a hydrophobic vent or a hole or some other means for allowing-air to escape whilst substantially preventing foam from escaping from the chamber. The chamber may have one or more flexible walls and may be substantially empty/airless in its initial state prior to filling with foam. In the latter case, the flexible chamber may be contained within a space defined by rigid walls of the plunger, in which case it may be preferable to have vents in the said rigid walls to allow air between the chamber walls and the said rigid plunger walls to escape when the chamber is filling with foam.

In an alternative arrangement, the waste chamber may simply comprise a bag located behind the face of the plunger, but with an inlet through the front face of the plunger whereby the bag communicates with the main chamber of the syringe. The bag is preferably inextensible.

The inlet to the chamber is preferably adjacent the syringe nozzle when the plunger is in its fully depressed state. The chamber may be substantially cylindrical with substantially rigid walls, in which case it may be defined by an end wall adjacent the syringe nozzle when the plunger is depressed, in which end wall the said inlet is located. Alternatively, the chamber may have no end wall, in which case the chamber comprises a back wall remote from the syringe nozzle and a cylindrical wall.

The second aspect of the invention also encompasses a syringe as defined above together with a source of foam, e.g. a pressurized canister adapted for generating foam, either in assembled form or in kit form.

A method of dispensing foam according to the second aspect and using a syringe as defined above may comprise the steps of:

(a) connecting a syringe as defined above to a source of foam or alternatively providing an assembly comprising a source of foam having an outlet connected to the syringe nozzle; and (b) dispensing a continuous flow of foam into the syringe from the source;

(c) whereby the flow of foam initially enters the waste chamber such that foam fills or substantially fills the said waste chamber; and (d) the flow of foam subsequently pushes the syringe plunger back in the syringe barrel and starts to fill the syringe.

According to a third aspect of the invention a syringe for dispensing foam comprises:

(a) a syringe barrel comprising a cylindrical side wall and a front end wall in which is located a syringe nozzle; and (b) a syringe plunger having an end face which seals against or surface of the cylindrical side wall of the syringe;

(c) wherein the side wall of the barrel is provided with an outlet at a position remote from the nozzle.

Preferably the end face of the syringe plunger, or a portion of it, makes an oblique angle with the longitudinal axis of the syringe barrel.

A waste container may be fitted to the outlet or connected to it via tubing. The waste container may have substantially rigid walls or may have one or more flexible walls. A hydrophobic vent or a vent hole may be provided in a wall of the waste container.

The third aspect encompasses an assembly or a kit comprising two or more of: a syringe as described above, a waste container as described above and a foam source (e.g. a pressurized canister adapted for generating foam).

The third aspect of the invention encompasses a method of using the apparatus described above comprising the steps of:

(a) connecting a syringe as defined above to a source of foam or alternatively providing an assembly comprising a source of foam having an outlet connected to the syringe nozzle, with the syringe plunger drawn back such that the syringe nozzle and syringe outlet communicate; and (b) dispensing a continuous flow of foam into the syringe from the source;

(c) whereby foam flows into the syringe and fills or substantially fills it, with an initial portion of the foam being directed out of the syringe outlet to waste.

Preferably, a waste container is fitted to the syringe outlet or connected to it by tubing, or such an arrangement is provided ready assembled. Also, preferably the syringe is held in a vertical orientation to help the exit of bubbles to waste. This helps large bubbles to rise and be ejected before too much foam is wasted.

Once it is determined that the foam passing out of the outlet is of substantially consistent, acceptable quality, the flow of foam from the generator is stopped and the plunger depressed to seal off the outlet from communication with the syringe nozzle. The waste chamber and the source may then be disconnected and the syringe full of foam is ready for use.

If the end face of the plunger is formed obliquely, this helps prevent dead spots in the flow of foam from the source to the outlet, thus helping to ensure that all or substantially all the poor quality foam is removed from the syringe without too much wasting of good foam. If there is any poor quality foam retained in the syringe, it is likely to be in the vicinity of the plunger face, e.g. if the foam is stiff or if the syringe is held vertical or at least with the nozzle pointing downwards at an angle throughout the procedure. Having the plunger face at an oblique angle to the end wall of the syringe barrel means that the syringe is never completely emptied of foam, and any poor foam will be retained in the space formed between the end wall of the barrel and the oblique-face of the plunger.

The sequence of operation may thus be:
1. Continuously dispense foam into the syringe with the plunger drawn back past the side outlet until all or substantially all foam of poor quality (either from the start up phase of the foam source or due to air pockets in the syringe or in any system interposed between the syringe and the source) has been driven out of the outlet.
2. Before disconnecting the syringe from the source of foam, cease generating or dispensing foam into the syringe.
3. Push the plunger past the side outlet.
4. Disconnect the foam source.

Further features and details of the invention will be apparent from the following description and from the accompanying drawings in which:

FIG. 1 is a schematic sectional view of a first embodiment of syringe and system;

FIG. 2 is a schematic sectional view of a second embodiment of syringe and system;

FIG. 3 is a schematic sectional view of a third embodiment of syringe and system;

FIG. 4 is a schematic sectional view of a fourth embodiment of syringe and system;

FIG. 5 is a schematic sectional view of a fifth embodiment of syringe and system;

FIG. 5a is a schematic sectional view of a modified version of the fifth embodiment;

Figure 6:
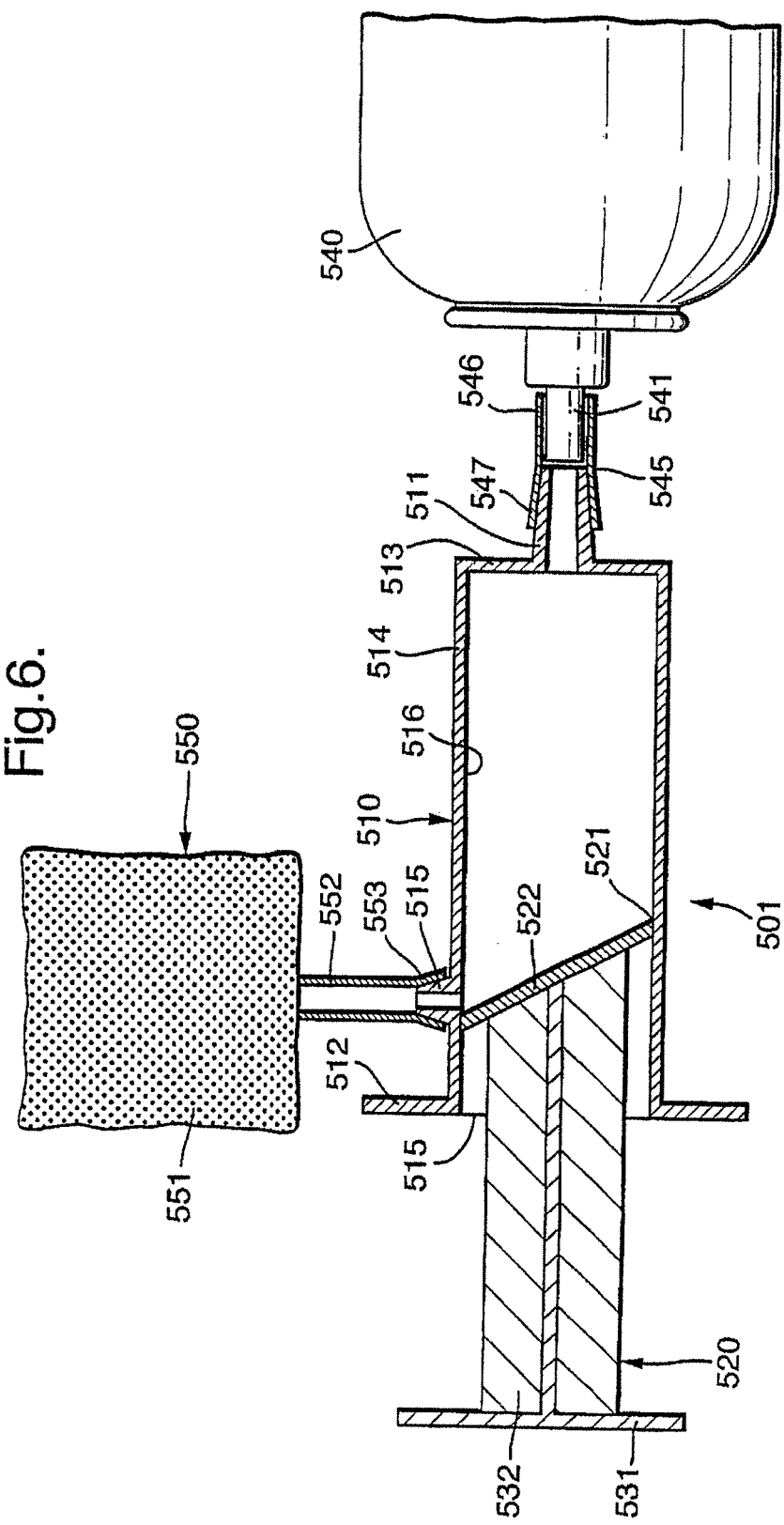
FIG. 6 is a sectional view of a sixth embodiment of syringe and system.

Referring firstly to FIG. 1, a system is shown for filling a syringe with a clinical grade foam made with a sclerosant liquid, e.g. 1% polidocanol solution, for injection into varicose veins. The canister 40 shown schematically in FIG. 1 is shown in more detail in the sectional view of FIG. 7. A dip tube 44 communicates with an internal valve 42 which functions in a conventional way to open the canister when it is depressed. Mounted on top of the valve is a stack of mesh elements 43 communicating with a canister nozzle 41, the whole mesh stack arrangement being slidably mounted such that the canister nozzle 41 may be depressed to open the valve 42.

The canister 40 contains sclerosant liquid as described above, together with a gas mixture comprising carbon dioxide and oxygen at 3 bar gauge pressure.

The syringe 1 comprises a barrel 10 which has a front end wall 13 in which is located a conventional luer nozzle 11, a cylindrical side wall 14 and an opening 15 at the back end. Finger grips 12 are located at the back end as is conventional. Received within an internal bore 16 of the barrel 10 is a plunger 20 with a seal formation 21 at the front end thereof which seals with the bore 16 of the barrel as is conventional.

The plunger 20 of formed of a plastics moulding having a front end wall 22 and a cylindrical wall 23. The back end of the plunger moulding has no wall but has a resilient plug 24 fitted therein. Located in the resilient plug 24 is an inlet 25 which includes a one way valve 26 of conventional design. Extending within the plunger 20 is a tube 27 which communicates between the inlet 25 and an outlet 28 in the front end wall 22 of the plunger 20. The outlet 28 is located such that it is in registry with the bore of the luer nozzle 11 when the plunger is fully received into the barrel 10.

The inlet 25 is designed to make a seal with the nozzle 41 of a pressurized canister 40 for generating foam. As described above, foam is dispensed when the canister nozzle 41 is depressed, thereby opening the internal valve 42 in the canister 40, and propelling gas and liquid through a stack of mesh elements 43 and out of the nozzle 41 as foam.

Fitted onto the front end of syringe is a waste container 50. The waste container comprises a flexible bag 51 of e.g. of inextensible film or foil. The container 50 is equipped with a rigid tube 52 communicating with the interior of the bag 51, with the walls of the bag sealed around the tube 52. The outer end of the tube 52 is formed as a female luer connector 53.

In operation, the syringe, with the plunger 20 in the fully depressed position as shown in FIG. 1, is fitted to the canister by inserting the canister nozzle 41 into the complementarily-formed plunger inlet 25. A waste container 51 is then fitted to the syringe nozzle 11 so as to seal around the nozzle.

The syringe 1 is then pushed towards the canister 40 by applying force to the syringe finger grips 12, whereby the canister nozzle 41 is pushed in so as to activate the canister valve and generate a flow of foam from the canister. Foam flows from the canister 40 into the inlet 25, past the valve 26, through the tube 27, out of the plunger outlet 28 and then out of the syringe nozzle 11 and into the waste contain 50.

Pressure on the syringe towards the canister is maintained so that the flow from the canister 40 is continuous. The initial portion of this flow consists of foam of inconsistent and poor quality; this foam is fed into the container 50 as described above, together with air from the tube 27 in the plunger and from the luer nozzle 11, and from any other dead spaces in the system. This air may become incorporated in the foam in which case the quality of the foam may be affected; whether or not this happens, the air is dispensed from the syringe nozzle 11 into the waste container 50.

The flexible walls of the waste container, which is initially substantially airless, allow it to expand as foam enters, until it can hold no more foam. As foam continues to flow from the canister 40, a back pressure is built up which soon becomes sufficient to overcome the friction between the plunger seal 21 and the inner surface 16 of the syringe barrel 10. The plunger 20 then moves back and the syringe barrel fills with substantially homogeneous, good quality foam.

The walls of the syringe barrel 10 are transparent, which allows the quality of the foam to be checked by the user. The user may be looking for homogeneity, bubble size, density or stiffness, all of which may be discerned to some degree by the naked eye: when the bubbles are microscopic, the foam may take on a smooth, white appearance. The volume of the waste container is about 10% of that of the syringe and this has been determined to ensure that both the initial quantity of poor foam together with any trapped air in the system can be dispensed into the container before the waste container becomes full. The visual check on the contents of the syringe could therefore be dispensed with, but is nevertheless desirable to ensure nothing has gone wrong.

Once a sufficient quantity of foam has been dispensed into the syringe, pressure on the canister nozzle is released, thereby shutting off the flow of foam. The waste container 50 may then be removed and the foam-filled syringe is ready for use. Use of the syringe 1 involves dispensing foam down a line to a cannula inserted into the venous system of a human patient. When the plunger 20 is depressed to dispense foam, it will be appreciated that the one way valve 26 on the plunger inlet 25 prevents flow of foam back out of the inlet.

A modification to this system is to provide a valve 54 in the tube 52 of the waste container 50. At the start of the filling process, this valve 54 is open; when foam is being delivered, the user may determine from visual inspection that the foam in the syringe is of acceptable quality even though the bag 51 is not yet full. In this case, the user may shut off the valve 54 so that the plunger starts to move back and the syringe to fill.

In another modification, the waste container 50 could comprise a rigid vessel, in which case a vent would be provided to allow displaced are to be exhausted as foam entered the container.

A second embodiment is shown in FIG. 2. Reference numerals for parts corresponding to parts of the first embodiment correspond, with the series starting at 101. In the second embodiment, the waste container 150 is incorporated within the plunger 120.

The syringe barrel 110 and its various parts are the same as for the first embodiment. The plunger 120 is almost the same as that of the first, embodiment as regards its external features, except that it has a small vent hole 130 in its cylindrical side wall—the operation of this feature will be described below. The inlet 125, fitted with a one-way valve 126, communicates with a waste container 150 located within a cavity in the plunger defined by the plunger walls 122, 123 and plug 124. The canister 140, shown schematically in FIG. 2, is the same as that of the first embodiment and the same as that shown in FIG. 7. The waste container 150 comprises an elongate bag 151 extending the length of the plunger. The inlet 125 is aligned so as to direct foam along the length of the bag 151 and thus fill the bag from the end 155 furthest from the inlet.

Adjacent the inlet 125 is a burst seal 156 in the wall of the bag 151. The burst seal 156 communicates with a tube 127, also located within the plunger, and which communicates in turn with an outlet 128 analogous to the outlet 28 in the first embodiment. In FIG. 2, the outlet 128 is shown as being slightly to one side of the syringe nozzle 111; alternatively, and preferably, the nozzle 111 and outlet 128 are in registry with each other.

The volume of the bag 151 is about 5-10% of the volume of the syringe barrel when the plunger is fully back. In use, similar to the first embodiment, the syringe is pressed against the canister with the canister nozzle 141 fitted to the inlet 125, whilst the plunger 120 is in its fully depressed state as shown. Foam is then dispensed from the canister 140, through the nozzle 125 and into the bag 151. The jet of foam issuing from the canister nozzle 125 passes down to the end 155 of the bag 151 and the bag fills from this end. As the bag fills from its initially airless state, it displaces air around it in the cavity defined in the plunger; this is released through the vent 130 in the side wall of the plunger. In a modification, the tube 157 extends from the nozzle 125 and terminates at the blind end of the bag 151. This allows "bad" foam to accumulate distal to the pressure break valve 156, so that when the break valve 156 is broken, only good quality foam flows through the tube 127 to the outlet 128.

Once the bag 151 is full of foam, the quality of foam being dispensed from the canister is consistently good. The volume of the bag is such that the inlet end of the bag will contain good foam. Any dead spaces in the inlet 125 and the canister nozzle 141 are now filled with good quality foam. However, the tube 127 still contains air.

At this point continued generation of foam by the canister causes a back pressure to build up in the waste bag 151, sufficient to burst the seal 156 on the bag. The flow of foam is then diverted through the opening created by bursting the seal 156 and then into the tube 127. Foam at the inlet end of the bag may be displaced and may pass into the tube 127, but as discussed above this foam will be of good quality.

Foam passing into the tube 127 drives out air from the tube and then passes out through the outlet 128 and syringe nozzle 111. When the user observes foam exiting the syringe nozzle 111, he or she puts a syringe nozzle cap 102 on the luer nozzle 111 to block the flow. The plunger then moves back and the syringe fills.

As with the first embodiment, when the syringe is full, generation of foam is stopped and the canister removed. Before delivering foam from the syringe into a patient, the nozzle cap 102 is removed. As with the first embodiment, the valve 126 prevents foam flowing back out of the inlet 125 when the plunger is depressed to deliver foam through the nozzle 111.

The second embodiment is not the preferred one, since the user still needs to expel a small quantity of waste foam from the nozzle of the syringe and, preferably, to monitor this foam to ensure its quality. However, the majority of the waste foam is contained and the arrangement is neater than that of the first embodiment since the bag is contained within the plunger.

A third embodiment is shown in FIG. 3. Again, similar parts are designated by numbers corresponding to those used in the descriptions of the first and second embodiments, the series starting at 200. The canister 240 is identical to that of the first and second embodiments, as shown in more detail in FIG. 7.

This embodiment is similar in most respects to the second, the waste container being rigid rather than flexible. The waste container 250 is an annular shape extending for most of the length of the plunger as shown in the Figure, apart from a flat cylindrical portion 257 at the inlet end. The container 250 is defined by the end and side walls 222, 223 and the bung 224 of the plunger, together with a central rigid tubular portion 227 of the plunger.

In the front end wall 222 of the plunger 220 are located hydrophobic vents 229. These are composed of a fine mesh or porous material such as a porous PTFE film. Their purpose is to allow air to pass through but not liquid (or foam).

Located in the region of the inlet end of the plunger 220 is a burst seal 256 which seals the interior of the container 250 from the interior of the tubular portion 227.

In use, the third embodiment works in an analogous manner to the second embodiment. Foam is generated by the canister when the syringe is pressed against it to depress the canister nozzle 241 in order to actuate the canister valve (see FIG. 7). Foam flows from the canister into the inlet 225 and is carried by its own momentum to the front and of the waste container 250, air being displaced through the hydrophobic vents 229.

Foam builds up in the container until it is full, the container being sized such that the foam in the region of the inlet 225 is of good quality. A back pressure accumulates and bursts the seal 256, allowing foam to pass down the central tube 227.

The remainder of the operation of the third embodiment is exactly as described for the second embodiment. This embodiment is not preferred, for similar reasons to those explained above in connection with the second embodiment. In addition to those issues, in the third embodiment the hydrophobic vents may become blocked with foam and prevent air escaping from the waste container 250.

A fourth embodiment is shown in FIG. 4. As before, reference numerals designating similar parts correspond, but with the sequence starting at 301. In this embodiment, unlike the first to third described above, the syringe is filled from the front, through the main syringe nozzle 311.

Figure 7:
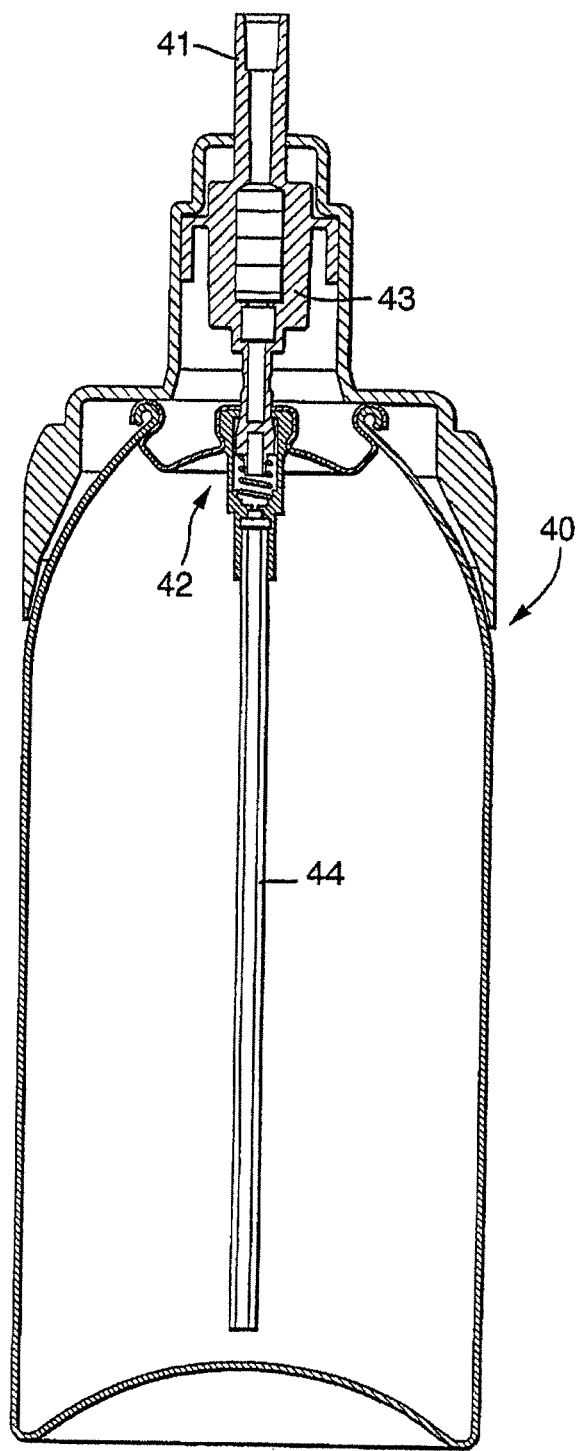
FIG. 7 is a sectional view of a pressurized canister for generating foam, which canister forms part of the first to sixth embodiments.

The barrel 310 of the syringe 301 is identical to that of previous embodiments, and is conventional. The canister 340 is identical to that of the first to third embodiments, as shown in FIG. 7.

A tubular connector 345 is provided to make a sealing connection between the canister nozzle 341 and the syringe luer nozzle 311. One end 346 of the connector is adapted to receive the canister nozzle 341 whilst the other is formed as a female luer connector 347 to fit the luer nozzle 311 of the syringe.

The plunger 320 is formed conventionally with a rear flange 331 to assist manual actuation, whilst the shaft 332 of the plunger is formed, also conventionally, with a cruciform section. At the front end of the plunger 320, a waste container 350 is located. The container 350 is defined by a relatively short cylindrical side wall 323, a front end wall 322 and a rear end wall 333. An inlet aperture 334 is provided in the front end wall 322 which is in registry with the syringe nozzle 311 when the plunger 320 is in its fully depressed position. Hydrophobic vents 329 are provided in the rear end wall 333 of the container 350. The external cylindrical surface of the container forms a seal with the internal surface 316 of the barrel 310. The front end face 322 of the container is equivalent to the front face of the plunger in the other embodiments.

In use, the syringe nozzle 311 is connected to the canister nozzle 341 by means of the connector 345 as shown in FIG. 4. The syringe is pressed against the canister 340, thereby causing foam to be generated by the canister as previously described in connection with the other embodiments. The foam flows into the syringe nozzle 311 and then into the waste container 350. Air in the waste container is displaced out though the hydrophobic vents 329 whilst foam is retained in the container.

The volume of the waste container is about 10% of that of the syringe. Once full, as with previous embodiments, it is reasonably certain that the foam will be of consistent, acceptable quality. At this point pressure will build in the syringe as foam continues to be generated by the canister. The plunger 320 will be pushed back and the syringe filled. It is possible that a little of the foam in the waste container 350 will leak out of the inlet aperture 334 into the main chamber of the syringe. However, the foam adjacent the inlet of the container 350 will be good quality foam and therefore this is not too important.

Once the syringe is full, all that is required is to stop the generation of foam and detach the syringe, which is ready for use.

Referring now to FIG. 5, a fifth embodiment is shown which is similar in most respects to the fourth. As before, reference numerals designating similar parts correspond, but with the sequence starting at 401. In this embodiment, a flexible waste bag 451 is provided within a chamber 458 of the syringe plunger 420.

The barrel 410, connector 445 and canister 440 are identical to the fourth embodiment described above. The plunger 420 is also identical to that of the fourth embodiment except for the front end of the plunger 420 which houses a waste container bag 451. The front of the plunger 420 is formed, similar the fourth embodiment, as a short hollow cylinder having a cylindrical side wall 423, front end wall 422 and rear end wall 433. In the front end wall is provided an inlet 434 which communicates a waste bag 451 located in a chamber 458 defined by the walls 422, 423, 433. The waste bag 451 is in a substantially collapsed state so that it contains little or no air. Provided in the rear end wall 433 of the chamber 458 are vent holes 429.

In use, the fifth embodiment operates almost identically to the fourth. Instead of entering a rigid waste container, foam from the canister enters a flexible waste bag 451 which, as it fills, displaces air from the chamber 458 through vents 429. When the waste bag is full, the syringe plunger is pushed back and the syringe fills with consistent, good quality foam. As with the fourth embodiment, once the syringe is full the canister is shut off and the syringe simply detached for use.

A modification of the fifth embodiment is shown in FIG. 5a, which illustrates only the syringe (the other elements being the same as for FIG. 5). The syringe comprises a conventional syringe barrel 410. The plunger 480 has a rear flange 481 to assist application of pressure by hand. The shaft of the plunger comprises four parallel shaft members 482. The front end of the member comprises an end wall member 483 with a sealing region 484 around its periphery for sealing against the internal surface 416 of the barrel. In the centre of the end wall is an inlet 485 which, when the plunger is depressed fully, is in registry with the luer nozzle 411 of the syringe.

Extending from the rear face of the plunger 480 is a boss 486 through which extends the inlet 485. The boss 486 terminates in a flange 487 around which an airless waste bag 451 is retained.

The operation of this modification is exactly the same as that of the fifth embodiment.

A sixth embodiment is shown in FIG. 6. The system shown comprises a canister of identical design to the first to fifth embodiments and shown in detail in FIG. 7. Also provided is a connector 545 of identical design to the connector described above in connection with the fourth and fifth embodiments.

As before, reference numerals designating similar parts correspond, but with the sequence starting at 501.

In this embodiment, an additional luer nozzle 515 is provided in the side wall 514 of the syringe barrel 510, towards the rear of the syringe, for dispensing waste foam. In all other respects the syringe barrel 510 is conventional and the same as in the other embodiments.

The plunger 520 has a conventional rear flange 531 and shaft 532 of cruciform section, as in the fourth and fifth embodiments. The end wall 522 of the plunger makes a seal 521 with the interior surface 516 of the barrel 510 as is conventional, but the wall is inclined at an oblique angle to the longitudinal axis of the syringe 501.

In use, the syringe is pressed against the canister as previously described and foam is dispensed into the syringe with the plunger in the fully depressed position (not the position shown in the Figure). Although not shown in the Figure, it will be appreciated that when the plunger is fully depressed, there will still be a space defined between the face of the plunger and the interior of the end wall of the syringe barrel. The initial poor quality foam will enter this space, but will not fill it since air will be trapped in the space. Once a back pressure has built up, the plunger 520 will move back and the syringe fill with foam.

When the plunger reaches the position shown in FIG. 6, it will stop moving back since the foam will have a low resistance path into the waste bag 551 which is substantially airless in its initial state. The poor quality foam initially dispensed into the syringe will be the first to pass into the waste bag, assisted by the inclined face of the plunger.

After a quantity of foam has been dispensed into the waste bag 551, the syringe is filled exclusively with consistent, good quality foam. The user may determine that this state has been reached by observing the foam through the transparent walls of the syringe barrel 510. Alternatively or in addition the user may wait until the waste bag is full at which point a back pressure will build up which the user may feel on the syringe plunger as it starts to move.

However this state is determined, the user then shuts off the canister, moves the syringe plunger the few millimeters necessary to close the second luer 515, then removes the canister and waste bag. The syringe full of foam is then ready for use.

In a modification of this embodiment, the waste container described above, with a predetermined volume, is omitted. The principle of waste foam, exiting a nozzle on the side of the syringe barrel applies whether a container is attached or not; it is therefore possible to omit it or to provide some other form of container which is not designed to fill and provide a back pressure indicating that sufficient foam has been wasted. In this modification, the user simply determines by observation when all the foam in the syringe barrel is of adequate quality, or alternatively wastes foam for a predetermined time, and then stops generation of foam and proceeds as before.

The invention claimed is:

1. A syringe for dispensing therapeutic foam from a source of foam comprising:
   (a) a syringe barrel having a nozzle and a bore to receive a syringe plunger; and
   (b) a syringe plunger having a front end and a back end, the front end of said syringe plunger having an internal waste container with substantially rigid walls, said waste container defined by a substantially rigid cylindrical side wall, a front end wall which forms a front end face of the plunger and a rear end wall, said walls arranged such that the external cylindrical side wall forms a seal with an internal surface of the syringe barrel;
   said waste container having an inlet aperture in the front end wall which is adjacent to the syringe nozzle when the plunger is fully depressed into the syringe barrel and through which foam can flow when the syringe is filled through the nozzle;
   the waste container further comprising a hydrophobic vent in the rear end wall of the waste container, which allows air to escape from the waste container while substantially preventing foam from escaping the waste container when the waste container is filled with foam from the source.

2. A syringe as claimed in claim 1 wherein the waste container comprises a bag with an inlet which is in communication with the inlet aperture of the waste container.

3. A syringe as claimed in claim 2 wherein the bag is substantially empty of air in its initial state prior to filling with foam.

4. A syringe as claimed in claim 2 wherein a wall or walls of the bag is/are substantially inextensible.

5. A kit for providing a syringe full of foam, the kit comprising a syringe as claimed in claim 1 together with a source of foam.

6. A kit as claimed in claim 5 wherein the source of foam is a pressurised canister containing liquid to be foamed and gas under pressure.

7. A method of dispensing foam using a syringe as claimed in claim 1 comprising the steps of:
   (a) connecting the syringe nozzle to a source of foam; and
   (b) dispensing a continuous flow of foam into the syringe from the source;
   (c) whereby the flow of foam initially enters the waste chamber such that foam fills said waste chamber; and
   (d) the flow of foam subsequently pushes the syringe plunger back in the syringe barrel and starts to fill the syringe.

* * * * *